United States Patent
Akiyama et al.

(10) Patent No.: US 10,865,133 B2
(45) Date of Patent: Dec. 15, 2020

(54) DENTAL GLASS AND DENTAL COMPOSITION

(71) Applicant: GC Corporation, Shizuoka (JP)

(72) Inventors: Shigenori Akiyama, Tokyo (JP); Ryosuke Yoshimitsu, Tokyo (JP); Satomi Tateiwa, Tokyo (JP); Katsushi Yamamoto, Tokyo (JP); Syouichi Fukushima, Tokyo (JP)

(73) Assignee: GC Corporation, Shizuoka (JP)

( * ) Notice: Subject to any disclaimer, the term of this patent is extended or adjusted under 35 U.S.C. 154(b) by 0 days.

(21) Appl. No.: 16/315,781

(22) PCT Filed: Jul. 4, 2017

(86) PCT No.: PCT/JP2017/024481
§ 371 (c)(1),
(2) Date: Jan. 7, 2019

(87) PCT Pub. No.: WO2018/012352
PCT Pub. Date: Jan. 18, 2018

(65) Prior Publication Data
US 2019/0151204 A1    May 23, 2019

(30) Foreign Application Priority Data
Jul. 15, 2016 (JP) ................................. 2016-140440

(51) Int. Cl.
| | | |
|---|---|---|
| *C03C 3/16* | (2006.01) | |
| *C03C 4/00* | (2006.01) | |
| *A61K 6/838* | (2020.01) | |
| *A61K 6/833* | (2020.01) | |
| *C03C 3/247* | (2006.01) | |
| *C03C 3/19* | (2006.01) | |
| *A61P 1/02* | (2006.01) | |

(52) U.S. Cl.
CPC .............. *C03C 4/0021* (2013.01); *C03C 3/16* (2013.01); *A61K 6/833* (2020.01); *A61K 6/838* (2020.01); *A61P 1/02* (2018.01); *C03C 3/19* (2013.01); *C03C 3/247* (2013.01); *C03C 2205/06* (2013.01)

(58) Field of Classification Search
CPC .......... A61K 6/30; A61K 6/831; A61K 6/833; A61K 6/836; A61K 8/838; A61K 6/887; A61K 8/889; C03C 3/16; C03C 3/19; C03C 3/247; C03C 12/00; C03C 8/06; C03C 8/08; C03C 4/0021; C03C 4/0007
See application file for complete search history.

(56) References Cited

U.S. PATENT DOCUMENTS

| | | |
|---|---|---|
| 5,296,026 A | 3/1994 | Monroe et al. |
| 6,692,532 B1 * | 2/2004 | Healy ................. A61L 24/0068 623/23.51 |
| 2004/0065228 A1 | 4/2004 | Kessler et al. |

FOREIGN PATENT DOCUMENTS

| | | |
|---|---|---|
| EP | 0473048 | 3/1992 |
| EP | 0809506 | 6/2002 |
| EP | 1113826 | 11/2005 |
| JP | H05-032517 | 2/1993 |
| JP | 2004-521135 | 7/2004 |
| JP | 2008-120681 | 5/2008 |
| JP | 2008-520565 | 6/2008 |
| WO | 97/27148 | 7/1997 |
| WO | 2006/055317 | 5/2006 |

OTHER PUBLICATIONS

Motohiro UO et al., "Na2O-CaO-P2O5-kei Suiyosei Glass no Sakusei to Saibo Dokusei Hyoka", Muki Rin Kagaku Toronkai Koen Yoshishu, 2007, vol. 17th, pp. 50 to 51.
Brauer, S. Delia et al., Solubility of glasses in the system P2O5-CaO-MgO-Na2O-TiO2: Experimental and modeling using artificial neural networks, J Non-Cryst Solid, 2007, vol. 353, No. 3, pp. 263-270.
International Search Report for PCT/JP2017/024481 dated Aug. 15, 2017.

* cited by examiner

*Primary Examiner* — Elizabeth A. Bolden
(74) *Attorney, Agent, or Firm* — IPUSA, PLLC

(57) ABSTRACT

A dental glass includes: phosphorus; sodium and/or potassium; and calcium, wherein the dental glass contains, in terms of oxide, phosphorus ($P_2O_5$) by greater than or equal to 40% by mass and less than or equal to 70% by mass, sodium and/or potassium ($Na_2O$, $K_2O$) by greater than or equal to 20% by mass and less than or equal to 40% by mass, and calcium (CaO) by greater than or equal to 1% by mass and less than or equal to 20% by mass, and wherein the dental glass does not substantially contain silicon and aluminum.

4 Claims, No Drawings

DENTAL GLASS AND DENTAL COMPOSITION

TECHNICAL FIELD

The present invention relates to a dental glass and a dental composition.

BACKGROUND ART

In a dental composition such as a dental cement, a dental composite resin, and a dental adhesive, a dental glass is occasionally blended. This is because, by blending a dental glass in a dental composition, not only an effect of enhancing the strength but also an effect due to ions in the dental glass can be obtained.

As an effect due to ions in the dental glass, specifically, for example, aluminum ions can be cured by reacting with an acid solution (glass ionomer cement). In addition, by being released in a mouth and absorbed by teeth, fluoride ions are expected to have effects of strengthening the teeth and preventing dental carries. Calcium ions and phosphate ions are also expected to have effects of remineralizing teeth and preventing dental carries by being absorbed by the teeth.

Therefore, as disclosed in, for example, Patent Document 1 to Patent Document 3, a dental glass containing calcium or phosphorus (also referred to as physiologically active glass composition, bioactive glass or the like) and a dental composition in which a dental glass is mixed are conventionally known.

PRIOR ART DOCUMENTS

Patent Documents

[Patent Document 1] Japanese National Publication of International Patent Application No. 2004-521135
[Patent Document 2] Japanese National Publication of International Patent Application No. 2008-520565
[Patent Document 3] Japanese Patent No. 5020833

DISCLOSURE OF THE INVENTION

Problems to be Solved by the Invention

However, in conventional dental glasses, the property of releasing calcium ion and phosphate ion is not necessarily high, and the effects of remineralizing teeth and preventing dental carries are not sufficient.

The present invention is made in view of the problem of conventional techniques described above, and an object in one aspect of the present invention is to provide a dental glass that is excellent in a property of releasing calcium ions and phosphate ions.

Means for Solving the Problem

According to one aspect of the present invention, a dental glass includes: phosphorus; sodium and/or potassium; and calcium, wherein the dental glass contains, in terms of oxide, phosphorus ($P_2O_5$) by greater than or equal to 40% by mass and less than or equal to 70% by mass, sodium and/or potassium ($Na_2O$, $K_2O$) by greater than or equal to 20% by mass and less than or equal to 40% by mass, and calcium (CaO) by greater than or equal to 1% by mass and less than or equal to 20% by mass, and wherein the dental glass does not substantially contain silicon and aluminum.

Effects of the Invention

According to one aspect of the present invention it is possible to provide a dental glass that is excellent in a property of releasing calcium ions and phosphate ions.

Embodiments for Carrying Out the Invention

In the following, an embodiment for carrying out the present invention will be described. The present invention is not limited to the following embodiment, and various modifications and substitutions can be made for the following embodiment without departing from the scope of the present invention.

[Dental Glass]

In the present embodiment, a configuration example of a dental glass will be described.

A dental glass according to the present embodiment can contain phosphorus; sodium and/or potassium; and calcium.

Further, it is possible to contain, in terms of oxide, phosphorus ($P_2O_5$) by greater than or equal to 40% by mass and less than or equal to 70% by mass; sodium and/or potassium ($Na_2O$, $K_2O$) by greater than or equal to 20% by mass and less than or equal to 40% by mass; and calcium (CaO) by greater than or equal to 1% by mass and less than or equal to 20% by mass.

Also, it is preferable not to substantially contain silicon and aluminum.

Because calcium ions and phosphate ions are expected to have effects of remineralizing teeth and preventing dental carries by being absorbed by the teeth, the inventors of the present invention have conducted earnest studies on a dental glass that is excellent in a property of releasing calcium ions and phosphate ions. As a result, the inventors of the present invention have found that a dental glass containing phosphorus (P); one or more kinds selected from sodium (Na) and potassium (K); and calcium (Ca) at a predetermined ratio enables to release a large quantity of ions such as calcium ions and phosphate ions, completed the present invention.

As described above, the dental glass according to the present embodiment can contain phosphorus (P), in terms of oxide ($P_2O_5$), by greater than or equal to 40% by mass and less than or equal to 70% by mass. This is because the solubility of the dental glass in water can be increased when the content of P is greater than or equal to 40% by mass in terms of oxide. However, in order to sufficiently secure the content of other components, the content of P is preferably less than or equal to 70% by mass in terms of oxide. Phosphate ions released from the dental glass have effects of remineralizing teeth and preventing dental carries. The content of P in the dental glass according to the present embodiment is more preferably greater than or equal to 53% by mass and less than or equal to 70% by mass in terms of oxide.

Also, the dental glass according to the present embodiment can contain sodium (Na) and/or potassium (K), in terms of oxide ($Na_2O$, $K_2O$), by greater than or equal to 20% by mass and less than or equal to 40% by mass. This is because the solubility of the dental glass in water can be increased by containing Na and/or K, in terms of oxide, by greater than or equal to 20% by mass and less than or equal to 40% by mass. However, in order to sufficiently secure the content of other components, the content of Na and/or K is preferably less than or equal to 40% by mass in terms of oxide. Sodium ions and/or potassium ions released from the dental glass have an effect of adjusting a pH value suitable for remineralizing teeth and preventing dental carries. The content of Na and/or K in the dental glass according to the present embodiment is more preferably greater than or equal to 25% by mass and less than or equal to 40% by mass in terms of oxide. Note that in a case of containing both Na and K, it is preferable that the total content of both components is in the above range in terms of oxides.

Also, the dental glass according to the present embodiment can contain calcium (Ca), in terms of oxide (CaO), by greater than or equal to 1% by mass and less than or equal to 20% by mass. This is because, when the content of Ca is greater than or equal to 1% by mass in terms of oxide, it is possible to secure a sufficient release amount of calcium ions from the dental glass. However, in order to sufficiently secure the content of other components, the content of Ca is preferably less than or equal to 20% by mass in terms of oxide. Calcium ions released from the dental glass have effects of remineralizing teeth and preventing dental carries. The content of Ca in the dental glass according to the present embodiment is more preferably greater than or equal to 2% by mass and less than or equal to 15% by mass.

Also it is preferable that the dental glass according to the present embodiment does not substantially contain silicon and aluminum. This is because if silicon and/or aluminum are contained, the solubility of the dental glass in water decreases. Note that not substantially containing it means not intentionally adding it in the dental glass, and does not exclude, for example, an impurity in a production step that is mixed as an inevitable component mixed. For example, it means that in terms of oxide, the respective contents of silicon and aluminum are less than 1% by mass. In particular, the total content of silicon and aluminum is preferably less than 1% by mass in terms of oxide.

The dental glass according to the present embodiment can also contain optional components in addition to the components described above.

The dental glass according to the present embodiment can contain, for example, strontium (Sr), in terms of oxide (SrO), by greater than or equal to 0% by mass and less than or equal to 20% by mass. When the dental glass according to the present embodiment contains Sr, a radiopacity can be added to the dental glass.

The dental glass according to the present embodiment can contain, for example, lanthanum (La), in terms of oxide ($La_2O_3$), by greater than or equal to 0% by mass and less than or equal to 20% by mass. When the dental glass according to the present embodiment contains La, a radiopacity can be added to the dental glass.

The dental glass according to the present embodiment can contain, for example, boron (B), in terms of oxide ($B_2O_3$), by greater than or equal to 0% by mass and less than or equal to 10% by mass. When the dental glass according to the present embodiment contains B, an antibacterial property can be added to the dental glass.

The dental glass according to the present embodiment can contain, for example, zinc (Zn), in terms of oxide (ZnO), by greater than or equal to 0% by mass and less than or equal to 10% by mass. When the dental glass according to the present embodiment contains Zn, an antibacterial property can be added to the dental glass.

The dental glass according to the present embodiment can contain, for example, silver (Ag), in terms of oxide (AgO), by greater than or equal to 0% by mass and less than or equal to 10% by mass. When the dental glass according to the present embodiment contains Ag, an antibacterial property can be added to the dental glass.

The dental glass according to the present embodiment can contain, for example, fluorine (F) by greater than or equal to 0% by mass and less than or equal to 20% by mass. When the dental glass according to the present embodiment contains F, an effect of preventing dental carries can be added to the dental glass.

Also it is preferable that the dental glass according to the present embodiment does not substantially contain sulfur (S). This is because in a case where the dental glass according to the present embodiment contains S, it may cause an odor in a mouth. Note that, as described above, not substantially containing it means not intentionally adding it in the dental glass, and does not exclude, for example, an impurity in a production step that is mixed as an inevitable component mixed. The content of S in the dental glass according to the present embodiment is preferably less than 1% by mass.

Also it is preferable that the dental glass according to the present embodiment does not substantially contain iron (Fe). This is because in a case where the dental glass according to the present embodiment contains Fe, it may cause tooth discoloration in a mouth. Note that, as described above, not substantially containing it means not intentionally adding it in the dental glass, and does not exclude, for example, an impurity in a production step that is mixed as an inevitable component mixed.

The content of Fe in the dental glass according to the present embodiment is preferably less than 1% by mass. The pH of the dental glass according to the present embodiment when dissolved in water is preferably greater than or equal to 5 and less than or equal to 11, and is more preferably greater than or equal to 6 and less than or equal to 10. This is because when the pH is less than 5 or exceeds 11 it is not suitable for use in a mouth.

Note that the pH when a dental glass is dissolved in water can be a pH after a dental glass pulverized to have an average particle diameter of 10 μm, the pulverized glass is dispersed in distilled water so as to have a concentration of 1% by mass (input dental glass mass), and stirred at an ambient temperature for 1 hour.

Here, the average particle diameter means a particle diameter at an integrated value 50% in a particle size distribution obtained by a laser diffraction/scattering method, and has a similar meaning in other parts of the present specification.

The solubility of the dental glass according to the present embodiment in water is preferably greater than or equal to 10%.

Note that the solubility of a dental glass in water can be evaluated by the following procedure.

First, a dental glass pulverized to have an average particle diameter of 10 μm is dispersed in distilled water so as to have a concentration of 1% by mass (input dental glass mass), and stirred at an ambient temperature for 1 hour. Next, undissolved glass powder is recovered with filter paper. Then, the mass of the undissolved dental glass after being dried (undissolved dental glass mass) is measured, and the solubility of the dental glass in water is calculated by the following formula (1).

(solubility of dental glass in water (mass %))=[(input dental glass mass)−(undissolved dental glass mass)]/(input dental glass mass)×100     Formula (1)

The method of producing the dental glass according to the present embodiment described above is not particularly limited. For example, a dental glass can be produced by weighting and mixing materials so as to make a predetermined composition dental glass, heating it to be greater than or equal to the melting point of the materials, melting it to be homogeneous, and thereafter rapidly cooling it by a process such as a process of putting the melt into water or a twin-roll process. Also, various glass producing methods such as a sol-gel method can be used. Note that the obtained dental glass may also be subjected to a pulverization treatment so as to have a desired particle diameter depending on the intended use. A preferable configuration example of the method of producing the dental glass according to the present embodiment will be described later below.

According to the dental glass according to the present embodiment, because of containing P, Na and/or K, and Ca to be at respective predetermined contents and not substantially containing silicon and aluminum, it is possible to make a dental glass whose pH when being dissolved in water is in a range suitable for use in a mouth and whose solubility in water is high and that is excellent in a property of releasing calcium ions and phosphate ions.

The dental glass according to the present embodiment can also be used, for example, as a component of a dental composition. That is, a dental composition containing the dental glass according to the present embodiment can be made. Note that examples of the dental composition include, but are not limited to, a dental cement (conventional resin-modified glass type ionomer cement, resin cement), a dental bonding agent, a dental primer, a dental coating material, a dental composite resin, a dental indirect composite, a CAD/CAM composite block, a temporary restorative material, a dental filler, a dentifrice, and the like.

In this case, components other than the dental glass contained in the dental composition are not particularly limited, and various components can be contained in accordance with the purpose or the like of the dental composition or the like.

Examples of components other than the dental glass that can be contained in the dental composition include a filler, a (meth)acrylate, a solvent, a polymerization initiator, a stabilizer, a pigment, and the like.

As the filler, for example, one or more kinds selected from silica such as fumed silica, alumina, hydroxyapatite, titanium oxide, yttrium oxide, zirconia, fluoroaluminosilicate glass, barium glass, lanthanum glass, strontium glass, quartz glass, and the like can be preferably used. Note that the filler may be treated, as needed, with a surface treatment agent such as a silane coupling agent.

Also, the above-described (meth)acrylate means various monomers, oligomers, or prepolymers of acrylate or methacrylate, and may have one or more methacryloyloxy groups or acryloyloxy groups.

As the solvent, one or more kinds selected from, for example, ethanol, propanol, methyl ethyl ketone, acetone, and the like can be preferably used.

According to the dental composition according to the present embodiment, because of containing the above-described dental glass, it is possible to make a dental composition that is excellent in a property of releasing calcium ions and phosphate ions.

[Method of Producing Dental Glass]

Next, a configuration example of a method of producing the dental glass according to the present embodiment will be described. Note that, by the method of producing the dental glass according to the present embodiment, the dental glass described above can be produced. Hence, a part of the description already described will be omitted.

In the method of producing the dental glass according to the present embodiment, the dental glass can be produced by melting a material composition and thereafter pulverizing the material composition.

As described above, the dental glass according to the present embodiment can contain phosphorus, sodium and/or potassium, and calcium. Therefore, the material composition can contain materials corresponding to phosphorus, sodium and/or potassium, and calcium.

Although a material corresponding to phosphorus is not particularly limited, for example, one or more kinds selected from phosphoric acid, sodium phosphate, potassium phosphate, calcium phosphate, strontium phosphate, sodium dihydrogen phosphate, and the like can be preferably used as the material corresponding to phosphorus. Note that two or more kinds selected from the above compound group may be used in combination.

Although a material corresponding to sodium is not particularly limited, for example, one or more kinds selected from sodium phosphate, sodium dihydrogen phosphate, sodium carbonate, sodium hydrogen carbonate, sodium fluoride, and the like can be preferably used as the material corresponding to sodium. Note that two or more kinds selected from the above compound group may be used in combination.

Although a material corresponding to potassium is not particularly limited, for example, one or more kinds selected from potassium phosphate, potassium fluoride, potassium carbonate, potassium bicarbonate, dipotassium hydrogenphosphate, and the like can be preferably used as the material corresponding to calcium. Note that two or more kinds selected from the above compound group may be used in combination.

Although a material corresponding to calcium is not particularly limited, for example, one or more kinds selected from calcium fluoride, calcium phosphate, calcium carbonate, calcium hydroxide, and the like can be preferably used as the material corresponding to calcium. Note that two or more kinds selected from the above compound group may be used in combination.

Also, as described above, the dental glass according to the present embodiment can contain optional components other than the above-described components. For example, it is possible to contain one or more kinds selected from strontium, lanthanum, boron, zinc, silver, fluorine, and the like. In a case where the dental glass according to the present embodiment contains such optional components, the material composition can contain materials corresponding to the optional components.

Although a material corresponding to strontium is not particularly limited, for example, one or more kinds selected from strontium fluoride, strontium hydroxide, strontium carbonate, strontium oxide, strontium phosphate, and the like can be preferably used as the material corresponding to strontium. Note that two or more kinds selected from the above compound group may be used in combination.

Although a material corresponding to lanthanum is not particularly limited, for example, one or more kinds selected from lanthanum fluoride, lanthanum oxide, and the like can be preferably used as the material corresponding to lanthanum. Note that two or more kinds selected from the above compound group may be used in combination.

Although a material corresponding to boron is not particularly limited, for example, one or more kinds selected from boron oxide, borax, boron phosphate, and the like can be preferably used as the material corresponding to boron.

Note that two or more kinds selected from the above compound group may be used in combination.

Although a material corresponding to zinc is not particularly limited, for example, one or more kinds selected from zinc oxide, zinc fluoride, and the like can be preferably used as the material corresponding to zinc. Note that two or more kinds selected from the above compound group may be used in combination.

Although a material corresponding to silver is not particularly limited, for example, one or more kinds selected from silver oxide, silver nitrate, silver fluoride, and the like can be preferably used as the material corresponding to silver. Note that two or more kinds selected from the above compound group may be used in combination.

Although a material corresponding to fluorine is not particularly limited, for example, one or more kinds selected from calcium fluoride, strontium fluoride, sodium fluoride, and the like can be preferably used as the material corresponding to fluorine. Note that two or more kinds selected from the above compound group may be used in combination.

The respective materials in a material composition may be mixed so as to correspond to the composition of a dental glass. For example, the respective materials can be weighed and mixed in accordance with the composition of the dental glass to prepare the material composition (material composition preparation step).

Then, the obtained material composition can be placed in, for example, a crucible, heated and fused at a temperature in accordance with the melting point of the materials or the like, for example, greater than or equal to 700° C. and less than or equal to 1500° C., and thereafter cooled (heating/cooling step).

Although the cooling rate at the time of cooling is not particularly limited, for example, rapid cooling is preferable by various rapid cooling means such as a twin-roll process as described above or a process of pouring out the melt onto a metal plate and pressing it.

After being cooled and solidified, the dental glass can be produced by pulverization to have a desired particle diameter (pulverizing step).

In addition to the above-described steps, the method of producing the dental glass according to the present embodiment may further include optional steps. For example, classification or the like can be carried out such that the particle size distribution of the obtained dental glass becomes a desired distribution.

EXAMPLES

Although specific Examples and Comparative Examples will be described in the following, the present invention is not limited to the examples.

First, the evaluation methods of the dental glasses produced in the following Examples and Comparative Examples will be described.

(Vitrification)

In each of the following Examples and Comparative Examples, a material composition was prepared by mixing materials for a dental glass, the prepared material composition was heated and melted, and thereafter rapidly cooled to an ambient temperature to prepare the dental glass. Then, the state of each prepared dental glass was visually confirmed and evaluated as "GOOD" when vitrification was confirmed, and "POOR" when it was not vitrified. Note that when it was not vitrified, it means that a dental glass could not be prepared, and thus the subsequent evaluation was not carried out.

(Solubility in Water)

The prepared dental glass was pulverized to prepare a pulverized glass having an average particle diameter of 10 μm. Subsequently, the pulverized glass is dispersed in distilled water to have a concentration of 1% by mass (mass of charged dental glass), and the mixture is stirred at an ambient temperature for 1 hour. Next, undissolved glass powder was recovered with filter paper, and dried. Thereafter, the mass of the undissolved dental glass after being dried (undissolved dental glass mass) was measured, and the solubility of the dental glass in water was calculated by the following formula (1).

(solubility of dental glass in water (mass %))=[(input dental glass mass)−(undissolved dental glass mass)]/(input dental glass mass)×100   Formula (1)

(ph After Being Dissolved in Water)

The prepared dental glass was pulverized to prepare a pulverized glass having an average particle diameter of 10 μm. Next, a pH, after the pulverized glass was dispersed in distilled water so as to have a concentration of 1% by mass and stirred at an ambient temperature for 1 hour, was measured as the pH after being dissolved in water.

Example 1

Phosphoric acid, calcium phosphate, and sodium carbonate as materials were weighed and mixed so as to have the composition indicated in Table 1. Then, the obtained mixture was placed in a platinum crucible, heated at 1100° C. in an air atmosphere and melted, then poured out on a stainless steel plate and rapidly cooled by being pressed by an iron to produce a dental glass.

Note that in Table 1, with respect to P, Na, K, Ca, Sr, B, Si, Al, La, Zn and Ag, the ratios in terms of oxides are indicated.

Example 2 to Example 8

Except that materials were weighed and mixed such that the dental glasses had the compositions indicated in Table 1 for respective Examples, the dental glasses were prepared and evaluated similarly to Example 1.

The results are indicated in Table 1.

Comparative Example 1 to Comparative Example 9

Except that materials were weighed and mixed such that the dental glasses had the compositions indicated in Table 1 for respective Comparative Examples, the dental glasses were prepared and evaluated similarly to Example 1.

The results are indicated in Table 1.

TABLE 1

|  |  | Example 1 | Example 2 | Example 3 | Example 4 | Example 5 | Example 6 | Example 7 | Example 8 | Comparative Example 1 |
|---|---|---|---|---|---|---|---|---|---|---|
| COMPOSITION OF DENTAL GLASS (MASS %) | $P_2O_5$ | 68.3 | 57.7 | 59.6 | 53.9 | 44.2 | 49.8 | 52.4 | 59.8 | 73.7 |
|  | $Na_2O$ | 28.1 | 25.1 | 33.4 | — | 23.8 | — | 21.0 | 39.0 | 21.8 |
|  | $K_2O$ | — | — | — | 32.1 | — | 33.0 | — | — | — |
|  | CaO | 3.6 | 5.3 | 1.0 | 4.3 | 6.4 | 2.2 | 3.4 | 1.2 | 2.9 |
|  | SrO | — | 10.3 | — | 8.4 | 8.6 | 4.6 | — | — | — |
|  | $B_2O_3$ | — | 1.6 | — | 1.3 | — | — | 3.6 | — | — |
|  | $SiO_2$ | — | — | — | — | — | — | — | — | — |
|  | $Al_2O_3$ | — | — | — | — | — | — | — | — | — |
|  | $La_2O_3$ | — | — | 4.5 | — | 17.0 | — | 17.5 | — | — |
|  | ZnO | — | — | 1.5 | — | — | 3.9 | — | — | 1.6 |
|  | AgO | — | — | — | — | — | 6.5 | — | — | — |
|  | F | — | — | — | — | — | — | 2.1 | — | — |
|  | Fe | — | — | — | — | — | — | — | — | — |
|  | S | — | — | — | — | — | — | — | — | — |
| EVALUATION RESULTS | VITRIFICATION | GOOD | GOOD | GOOD | GOOD | GOOD | GOOD | GOOD | GOOD | GOOD |
|  | SOLUBILITY IN WATER | 78.0% | 28.0% | 88.0% | 56.0% | 21.0% | 89.0% | 15.0% | 100.0% | 32.0% |
|  | pH AFTER BEING DISSOLVED IN WATER | 7.3 | 7.5 | 8.7 | 7.0 | 8.4 | 6.8 | 8.4 | 9.6 | 3.1 |

|  |  | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|---|
| COMPOSITION OF DENTAL GLASS (MASS %) | $P_2O_5$ | 68.7 | 35.4 | 42.6 | 47.5 | 67.0 | 53.1 | 6.6 | 50.1 |
|  | $Na_2O$ | — | 33.8 | — | — | 16.2 | 8.4 | 30.6 | — |
|  | $K_2O$ | — | — | 56.4 | 15.5 | — | — | — | 32.3 |
|  | CaO | 31.3 | 6.2 | 1.0 | 10.1 | 7.2 | 2.5 | 15.8 | — |
|  | SrO | — | — | — | 26.9 | — | — | — | — |
|  | $B_2O_3$ | — | — | — | — | 4.8 | 19.3 | — | — |
|  | $SiO_2$ | — | — | — | — | — | — | 47.0 | — |
|  | $Al_2O_3$ | — | — | — | — | — | — | — | 11.4 |
|  | $La_2O_3$ | — | — | — | — | — | 9.6 | — | — |
|  | ZnO | — | — | — | — | 4.8 | — | — | 6.2 |
|  | AgO | — | — | — | — | — | 5.2 | — | — |
|  | F | — | 24.6 | — | — | — | 1.9 | — | — |
|  | Fe | — | — | — | — | — | — | — | — |
|  | S | — | — | — | — | — | — | — | — |
| EVALUATION RESULTS | VITRIFICATION | GOOD | POOR | POOR | GOOD | GOOD | GOOD | GOOD | GOOD |
|  | SOLUBILITY IN WATER | 8.0% | — | — | 2.6% | 7.1% | 1.3% | 2.4% | 2.6% |
|  | pH AFTER BEING DISSOLVED IN WATER | 3.9 | — | — | 7.2 | 3.0 | 2.5 | 11.8 | 7.5 |

According to the results indicated in Table 1, it was confirmed that in each of Example 1 to Example 8, the solubility in water was high and greater than or equal to 10%. Accordingly, the dental glasses could be confirmed as being excellent in a property of releasing ions such as calcium ions and phosphate ions contained in the dental glasses for the respective Examples. Also, the pH after being dissolved in water was in a range of greater than or equal to 5 and less than or equal to 11, and the dental glasses could be confirmed as being applicable into a mouth.

In contrast, Comparative Example 2 and Comparative Examples 5 to 9 had the solubility in water less than 10%, and could be confirmed as not having a sufficient solubility in water. Therefore, the dental glasses could be confirmed as being inferior in a property of releasing ions such as calcium ions and phosphate ions.

Also, in Comparative Example 1, although the solubility in water was 32% and high, the pH after being dissolved in water was 3.1 and very low, Comparative Example 1 could be confirmed as not being applicable into a mouth.

In Comparative Examples 3 and 4, vitrification could not be confirmed. That is, dental glass could not be obtained.

Although dental glasses and dental compositions have been described above with reference to the embodiment, the examples, etc., the present invention is not limited to the embodiments, the examples, etc. described above. Various modifications and changes can be made within the scope of the present invention recited in the claims.

The present application is based on and claims priority to Japanese Patent Application No. 2016-140440, filed on Jul. 15, 2016, the entire contents of Japanese Patent Application No. 2016-140440 are hereby incorporated herein by reference.

The invention claimed is:

1. A dental glass comprising:
phosphorus;
sodium and/or potassium; and
calcium,
wherein the dental glass contains, in terms of oxide,
phosphorus ($P_2O_5$) by greater than or equal to 40% by mass and less than or equal to 70% by mass,
sodium and/or potassium ($Na_2K_2O$) by greater than or equal to 20% by mass and less than or equal to 40% by mass,
calcium (CaO) by greater than or equal to 1% by mass and less than or equal to 6.4% by mass, and wherein the dental glass does not substantially contain, silicon and aluminum.

2. A dental composition comprising the dental glass according to claim 1.

3. A dental glass comprising:
phosphorus;
sodium and or potassium; and
calcium,
wherein the dental glass contains, in terms of oxide,
phosphorus ($P_2O_5$) by greater than or equal to 40% by mass and less than or equal to 70% by mass,
sodium and/or potassium ($Na_2O$, $K_2O$) by greater than or equal to 25% by mass and less than or equal to 40% by mass, and
calcium (CaO) by greater than or equal to 1% by mass and less than or equal to 20% by mass, and
wherein the dental glass does not substantially contain silicon and aluminum.

4. A dental composition comprising:
a dental glass; and
a (meth)acrylate,
wherein the dental glass contains, in terms of oxide,
phosphorus ($P_2O_5$) by greater than or equal to 40% by mass and less than or equal to 70% by mass,
sodium and/or potassium ($Na_2O$, $K_2O$) by greater than or equal to 20% by mass and less than or equal to 40% by mass, and
calcium (CaO) by greater than or equal to 1% by mass and less than or equal to 20% by mass, and
wherein the dental glass does not substantially contain silicon and aluminum.

* * * * *